(12) United States Patent
Knöpfle et al.

(10) Patent No.: US 7,682,361 B2
(45) Date of Patent: Mar. 23, 2010

(54) SYSTEM INCLUDING A SELF-RETAINING IMPLANT AND A DEVICE FOR SECURING THE IMPLANT AND A METHOD OF USING THE SAME

(75) Inventors: Christian Knöpfle, Donaueschingen (DE); Karl Greiner, Mühlheim (DE); Thorsten Frank, Tuttlingen (DE); Hans-Urs Eckerle, Freiburg i. Br. (DE)

(73) Assignee: Stryker Leibinger GmbH & Co KG, Freiburg (DE)

( * ) Notice: Subject to any disclaimer, the term of this patent is extended or adjusted under 35 U.S.C. 154(b) by 0 days.

(21) Appl. No.: 09/921,233

(22) Filed: Aug. 1, 2001

(65) Prior Publication Data

US 2002/0156477 A1 Oct. 24, 2002

(30) Foreign Application Priority Data

Apr. 24, 2001 (DE) .............................. 201 07 039 U

(51) Int. Cl.
*A61B 17/58* (2006.01)
(52) U.S. Cl. ......................................... 606/75; 606/99
(58) Field of Classification Search .................. 606/75, 606/72, 69, 70, 86, 104, 151, 331, 916, 329, 606/96, 98, 99; 29/243.56; 411/61, 508
See application file for complete search history.

(56) References Cited

U.S. PATENT DOCUMENTS

| 2,065,659 | A | * | 12/1936 | Cullen | 27/21.1 |
| 5,501,685 | A | * | 3/1996 | Spetzler | 606/75 |
| 5,549,620 | A | * | 8/1996 | Bremer | 606/151 |
| 5,709,682 | A | * | 1/1998 | Medoff | 606/60 |
| 5,741,268 | A | | 4/1998 | Schütz | 606/104 |
| 5,904,683 | A | * | 5/1999 | Pohndorf et al. | 606/287 |
| 5,916,217 | A | * | 6/1999 | Manthrop et al. | 606/75 |
| 5,964,762 | A | | 10/1999 | Biedermann et al. | 606/69 |
| 6,010,513 | A | | 1/2000 | Törmälä et al. | 606/142 |
| 6,168,596 | B1 | * | 1/2001 | Wellisz et al. | 606/69 |

(Continued)

FOREIGN PATENT DOCUMENTS

DE 19907354 A1 9/2000

OTHER PUBLICATIONS

European Search Report, Application No. EP-02 00 4363.4-23181.

(Continued)

*Primary Examiner*—Pedro Philogene
(74) *Attorney, Agent, or Firm*—Howard & Howard Attorneys PLLC

(57) ABSTRACT

The invention relates to a self-retaining implant for fixing a bone cover or a bone fragment in an opening in a skull bone. The implant comprises a support element with an upper side and an lower side facing the bone cover. Arranged on the lower side of the support element is an extension, which supports a spike preferably extending parallel to the support element. The spike can be driven laterally into the bone cover or bone fragment by means of a driving-in device according to the invention. The driving-in device according to the invention comprises a receiving element for the implant. A driving-in mechanism for driving the implant into the bone cover or bone fragment can be coupled with the receiving element.

15 Claims, 5 Drawing Sheets

U.S. PATENT DOCUMENTS

| | | | |
|---|---|---|---|
| 6,190,389 B1 * | 2/2001 | Wellisz et al. | 606/69 |
| 6,197,037 B1 * | 3/2001 | Hair | 606/151 |
| 6,302,884 B1 * | 10/2001 | Wellisz et al. | 606/69 |
| 6,458,133 B1 * | 10/2002 | Lin | 606/69 |
| 6,511,482 B1 * | 1/2003 | Wellisz et al. | 606/69 |
| 6,620,165 B2 * | 9/2003 | Wellisz | 606/69 |
| 6,969,391 B1 * | 11/2005 | Gazzani | 606/75 |

OTHER PUBLICATIONS

Translation of Supplemental Sheet B from the European Search Report identifying a Lack of Unity of Invention in the corresponding European Application.

* cited by examiner

SYSTEM INCLUDING A SELF-RETAINING IMPLANT AND A DEVICE FOR SECURING THE IMPLANT AND A METHOD OF USING THE SAME

This application claims priority to German Application No. 201 07 039.1 filed Apr. 24, 2001.

BACKGROUND OF THE INVENTION

1. Technical Field of the Invention

The invention relates to an implant for attaching a bone cover or bone fragment, and more particularly for fixing a bone cover or a skull bone fragment removed in a craniotomy to a skull cap. The invention also relates to a device for securing the said implant to the bone cover or bone fragment.

2. Description of the Prior Art

Within the framework of skull operations, bone covers, i.e. plate-shaped bone parts, are often sawn out of the skull bone. At the end of the operation, it is necessary to fix these bone covers again in the resulting opening in the top of the skull, so that the bone cover can heal into its old position again. A comparable problem arises when skull bone fragments need to be fixed in the region of the top of the skull.

Various implants have been proposed for attaching bone covers or skull bone fragments. Thus, implants are known which comprise two screw holes. In a first step, implants of this type are secured by means of screws to the bone cover, for example, which is to be fixed in place. Subsequently, the implants screwed to the bone cover are additionally securely screwed to the skull bone. As a result of the fact that it is firstly necessary to secure each individual implant by means of a screw in each case to the bone cover and then to the skull bone, the fixing of the bone cover is very time-consuming. In order to reduce the time outlay associated with the fixing of a bone cover, self-retaining implants have been proposed.

A self-retaining implant of this type is known, for example, from DE 199 07 354 A1. This implant is a clamp-like element, which is placed onto the bone cover which is to be fixed. To this end, the implant comprises two contact arms, which are arranged spaced apart from one another and in the fitted state of the implant engage around the bone cover. In this respect, the first of the two contact arms contacts the upper side of the bone cover and the second of the two contact arms contacts the underside.

A disadvantage in a clamp-like implant of this type is that it is awkward to handle. The awkward handling is first and foremost a result of the fact that different bone covers are not always of the same thickness and the thickness of a single bone cover may even vary. A further disadvantage is that the contact arm resting against the underside of the bone cover rests upon the flaps of the meninges once the bone cover is secured and under certain circumstances may damage the flaps.

It is the object of the invention to provide an implant system which comprises a self-retaining implant offering simplified handling.

SUMMARY OF THE INVENTION

This object is attained according to the invention by an implant system which comprises a self-retaining implant with a spike which can be laterally driven into the bone cover or bone fragment as well as a driving-in device for the said implant.

The self-retaining implant comprises a support element with an upper side and a lower side facing the bone cover or bone fragment. Arranged on the lower side of the support element is an extension, which supports at least one spike extending in the direction of the bone cover. The spike is laterally driven into the bone cover or bone fragment.

According to a first variant, the driving-in device comprises a force-transmitting element in the form of e.g. a holding or receiving element for the self-retaining implant, as well as a driving-in mechanism, which can be coupled with the force-transmitting element, for driving-in the implant, preferably the at least one spike of the implant, laterally into the bone cover or bone fragment. In this respect, the driving-in mechanism can be coupled with a force-receiving surface coupled with the force-transmitting element in such a manner that the driving-in force is transmitted by the driving-in mechanism into the force-receiving surface, from here into the force-transmitting element and from the force-transmitting element into the implant. According to a second variant of the driving-in device, there is no driving-in mechanism. In this case, the driving-in force is directly introduced, for example by means of a hammer-like tool, into the force-receiving surface, which is coupled with e.g. a receiving element for the implant in a force-transmitting manner.

The self-retaining implant according to the invention is not secured by pushing onto the bone cover, but is secured by means of one or more spikes laterally driven into the bone cover or bone fragment. The driving-in of the at least one spike of the implant is preferably effected by using a driving-in device according to the invention, which to this end may comprise a suitable driving-in mechanism. In practice, it has been found that a driving-in of the self-retaining implant, in particular with the use of a driving-in device according to the invention, is particularly advantageous from the point of view of handling. The connection between the implant and the bone cover or bone fragment resulting from the driving of the spike of the implant into, for example, the spongy region or cortical region of the bone cover or bone fragment is extremely stable and reliable.

The at least one spike of the self-retaining implant is arranged relative to the support element in such a manner that it can be reliably driven into the bone cover or bone fragment and ensures good anchoring of the implant. To this end, the spike preferably extends substantially parallel to the support element. However, the spike may also be inclined relative to the support element, so long as the spike can be driven in to a sufficient depth. The transition between the extension and the spike arranged on the extension may be continuous, so that no defined border is visible between the extension and the spike. However, according to a preferred embodiment, the spike projects from the extension at an angle of, for example, 90°.

The extension expediently forms an angle of between 45° and 135° with the implant element. Preferred is an extension which extends substantially at right angles to the support element. In this case, the extension can function as an abutment, which allows for precise driving-in of the spike. In other words: as soon as the extension comes to rest against lateral regions of the bone cover or bone fragment, it prevents further driving-in of the spike. In addition, an analysis of the position of the extension relative to a lateral region of the bone cover or bone fragment provides a visual assessment as to whether the spike of the implant has been driven in to a sufficient depth.

According to a preferred embodiment, the extension is arranged relative to the support element in such a manner that the support element and the extension essentially form a T-shaped structure in cross section. In this respect, the support element corresponds to the cross beam of the T and the extension corresponds to the longitudinal beam thereof. The extension thus divides the support element into two support arms extending in opposite directions. The first of the two support arms extends in the direction of the bone cover or bone fragment and the second of the two support arms in the direction of the skull bone. This type of design of the implant is advantageous, since the support arm extending in the direction of the bone cover, for example, and resting upon the upper side of the bone cover, together with the spike driven into the bone cover, allows for particularly reliable securing of the implant to the bone cover. In addition, the support arm cooperating with the bone cover can be advantageously used as a guide during the positioning and driving in of the implant.

It is, however, also possible to dispense with the support arm cooperating with the bone cover or bone fragment. Thus, instead of having a T-shaped design, the implant could also have a Z-shaped structure, for example, the upper cross beam of the Z functioning as a support element on the skull bone and the lower cross beam forming the spike.

The support element preferably has a flat, e.g. strip-shaped form. The underside of the support element can be concave or spherically curved at least in sections in order to ensure good adaptation of the implant to the curvature of the skull. Expediently, the support element of the implant is flexible at least in certain regions, in order to allow for individual adaptation of the implant to the curvature of the skull.

The spike of the implant which is to be driven in is arranged, for example, at an end of the extension remote from the support element. The spike can be designed in various ways. Thus, it is possible, for example, to provide a spike in the form of one or more spurs or a saw tooth structure. However, the spike preferably has a flat, triangular structure. In order to facilitate the driving-in of the spike, the spike can be provided with sharpened edges. The length of the spike can be freely selected within a wide range, so long as sufficiently reliable anchoring of the implant is guaranteed.

At its end opposite the spike, the support element may comprise a screw hole to allow for fixing of the bone cover or bone fragment provided with one or more implants to the skull bone by means of screws. In the case of a support element with two or more support arms, the screw hole is consequently constructed in the support arm which cooperates with the skull bone. The support element preferably has a locally increased thickness in the region of the screw hole. In this respect, the thickness of the support element in the region of the screw hole can be selected in such a manner that the screw head can be partially or fully recessed in the screw hole. This is advantageous for cosmetic reasons. In contrast, in the region of the support element outside the screw hole, the thickness of the support element can be markedly reduced. The interior of the screw hole is expediently spherically curved in order to allow for the recessing of bone screw heads having a corresponding spherical curvature.

The implant according to the invention can be driven into the bone cover or bone fragment in different ways. This is possible in a particularly simple manner using the driving-in device according to the invention comprising a driving-in mechanism. The driving-in mechanism can be constructed in such a manner that it allows for the application of a striking force upon a receiving or holding element provided for the implant. To this end, the driving-in mechanism can comprise a striking element, which is displaceable against a spring force. By means of the spring force, the striking element can be prestressed in the driving-in direction, the striking force being actuated by a sudden reduction in the prestressing.

The striking element is preferably formed by a first carriage guided coaxial to the receiving element. Guidance for the first carriage can be formed, for example, by a bolt arranged coaxial to the receiving element. The receiving element can be connected to the bolt or another stationary component of the driving-in device in such a manner that the receiving element is displaceable in the axial direction to a limited degree.

The driving-in device expediently comprises an operating mechanism for the driving-in mechanism. In the case of a driving-in mechanism which comprises a striking element displaceable against a spring force, the force required for the displacement of the striking element is preferably applied by means of the operating mechanism. To this end, the operating mechanism can be actuated with the aid of an electric motor or one or more fingers.

For the coupling of the operating mechanism with the striking element, i.e. for the prestressing of the striking element, for example, a coupling device can be provided. The coupling device comprises a driver, for example, for taking along the striking element. In cases where a coupling device is present, a corresponding decoupling device is expediently provided, which allows for a decoupling of the operating mechanism and striking element in order to activate the striking force.

According to a particularly preferred embodiment, the driving-in device according to the invention has a gun-like construction. This type of design allows for particularly ergonomic and reliable driving in of the implants. Other designs of the driving-in device according to the invention are, however, also conceivable. Thus, the driving-in device can have a substantially cylindrical form, for example.

A driving-in device having a gun-like design typically comprises a gun body and a gun barrel. The gun body can comprise a gun handle as well as a housing connected to the handle for accommodating the driving-in mechanism. The operating mechanism for the driving-in mechanism can be constructed as a finger-operated gun trigger. The gun trigger is preferably coupled with a second carriage displaceable against a spring force. In this case, the coupling device described above can be functionally arranged between the first and second carriages.

In the case of a gun-like design of the driving-in device, it is possible to arrange the receiving element for the implant in the manner of a piston barrel in relation to the gun body. This type of arrangement of the receiving element allows for particularly simple positioning of the implant, which is to be driven into place, relative to the bone cover or bone fragment.

The receiving element can be provided with a self-locking mechanism for the implant, so that the implant can be removed directly from the cartridge provided for the implant by means of the driving-in device. It is therefore unnecessary to touch the implant with the fingers during the entire securing procedure of the implant. This is desirable for ergonomic reasons.

DESCRIPTION OF THE DRAWINGS

An embodiment of the implant and an embodiment of the device will be explained in further detail in the following with the aid of several drawings, in which.

DESCRIPTION OF PREFERRED EMBODIMENTS OF THE INVENTION

Figure 1:
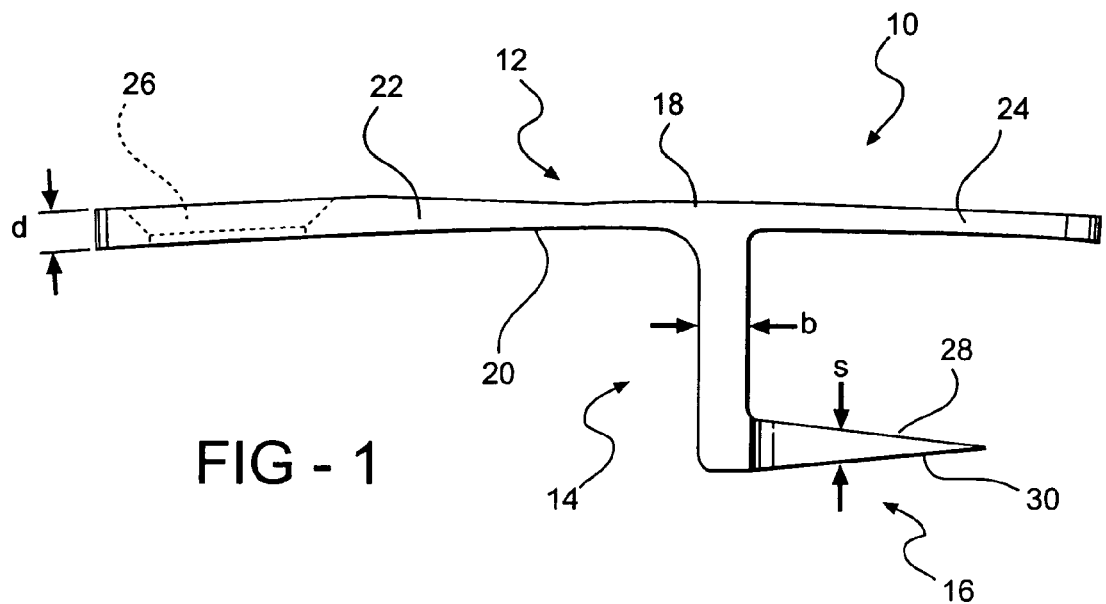
FIG. 1 is a side view of an embodiment of the implant according to the invention.

FIG. 1 is a side view of an embodiment of a self-retaining implant 10 according to the invention. The implant 10 comprises a support element 12, an extension 14 connected to the support element 12 and a flat spike 16 connected to the extension 14.

The support element 12 comprises an upper side 18 and a lower side 20. Following implantation, the lower side 20 contacts a bone cover or bone fragment, not shown in FIG. 1, as well as a skull bone, also not shown in FIG. 1. In order to ensure a implant of the lower side 20 which is as free of clearance as possible, the lower side 20 is spherically curved. The radius of curvature R measures 79.5 mm.

The support element 12 according to FIG. 1 is formed by two support arms 22, 24. In the implanted state of the implant 10, the left support arm 22 in FIG. 1 rests upon the skull bone and the right support arm 24 in FIG. 1 rests upon the bone cover, for example. The length ratio between the left support arm 22 and the right support arm 24 can be varied by means of the position of the extension 14 relative to the two support arms 22, 24. In the illustration according to FIG. 1, the left support arm 22 has a somewhat greater length than the right support arm 24.

The left support arm 22 is provided at its end remote from the spike 16 with a screw hole 26. In the region of the screw hole 26, the support element 12 has its maximum thickness d of approximately 0.5 mm. This thickness has been selected in order to allow for a cosmetically advantageous recessing of a bone screw head in the support element 12. In regions remote from the screw head 26, the support element 12 has a reduced thickness of, typically, 0.3 mm. This reduced thickness is selected in such a manner that the support element can be slightly bent in regions outside the screw hole. By bending the support element 12, the lower side 20 can be individually adapted to the curvature of the bone cover or skull bone.

The extension 14 of the implant 10 is secured to the lower side 20 of the support element 12 and extends substantially at right angles to the support element 12. Together, the support element 12 and the extension 14 form a T-shaped structure. In this respect, the support element 12 represents the cross beam of the T-shaped structure and the extension 14 the longitudinal beam.

The width b of the extension 14 needs to be small, so that the bone gap between the bone cover or the bone fragment and the skull bone can be kept to a minimum. The widths b are expediently less than one millimetre, for example 0.6 mm. By means of the implant 10, the bone cover or bone fragment can be positioned in the skull bone in such a manner that the bone gap along the contour of the bone cover or bone fragment is constant. However, in order to ensure faster growth of the bone cover or bone fragment, the bone cover or bone fragment can also be fixed by means of the implant 10 in such a manner that it has contact with the skull bone in certain areas.

When the support element 12 or the extension 14 is loaded with the driving-in force, which acts to the right in FIG. 1, the driving-in force is to be transmitted from the extension 14 to the spike 16. The spike 16 is constructed at the end of the extension 14 lying opposite the support element 12. It can be clearly seen in FIG. 1 that the spike extends perpendicular to the extension 14 and substantially parallel to the support element 12. The thickness s of the spike 16 gradually decreases as its distance from the extension 14 increases. The edges 28, 30 of the spike 16 are sharpened in order to facilitate the driving of the spike into the bone cover or bone fragment.

Figure 2:
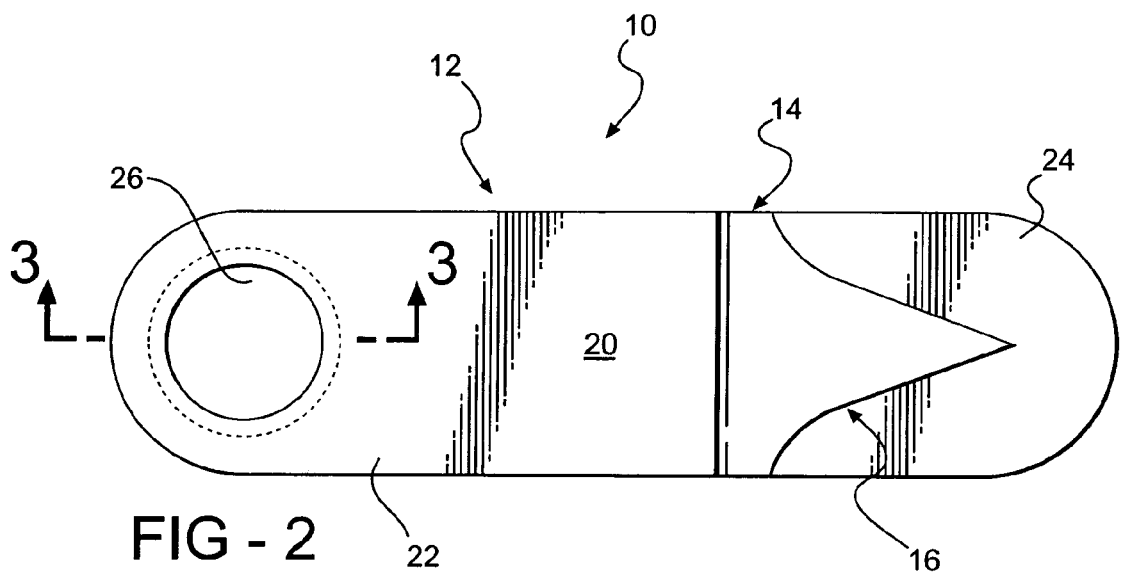
FIG. 2 is a plan view of the underside of the implant according to FIG. 1 facing the bone plate.

In FIG. 2, the implant 10 according to FIG. 1 is shown in a plan view of the underside 20 of the support element 12. As can be seen in FIG. 2, the support element 12 comprises a substantially strip-shaped form with rounded ends. The spike 16 is flat and triangular in design and can therefore be fitted with a comparatively low driving-in force. Alternative designs of the spike 16 are also conceivable. Thus, the spike 16 could be additionally provided, for example, with barb-like structures in order to improve the anchoring of the spike 16 in the spongy region.

Figure 3:
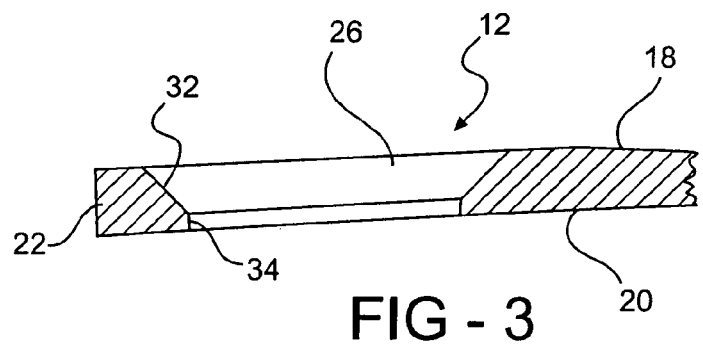
FIG. 3 is a sectional view through the support element of the implant according to FIGS. 1 and 2 in the region of a screw hole.

FIG. 3 is a section through the implant illustrated in FIG. 2 in the region of the screw hole 26. The interior of the screw hole 26 comprises a spherically curved region 32, which in the direction of the underside 20 opens into a short, cylindrical region 34. The spherically curved region 32 allows correspondingly shaped bone screw heads to be recessed in the support element 12.

The implant 10 according to FIGS. 1 to 3 is self-retaining, since it can be secured without securing elements such as screws, nails, etc. to a bone cover, for example. In contrast to the clamp-like implants of the state of the art, the retaining force of the implant 10 is substantially independent of the thickness of the bone cover. It is therefore possible to ensure a secure anchoring of the implant according to the invention even in the case of small bone cover thicknesses. The implant 10 is driven laterally into the bone cover or into the bone fragment. The anchoring of the implant 10 therefore requires no elements resting against the underside of the bone cover or bone fragment, so that damage to the meninges flaps by the implant 10 is ruled out.

The length of the extension 14, i.e. the distance between the spike 30 and the support element 12, is typically selected in such a manner that the implant 10 can be securely anchored in the case of bone cover thicknesses up to 3.5 mm. By preparing implants 10 with shorter extensions 14, it is also possible to fix bone covers with a thickness of less than 3.5 mm. The implant 10 is manufactured from biocompatible TiAl6V4. However, the implant 10 can also be made entirely or partially of a reabsorbable material instead of a metal.

Figure 4:
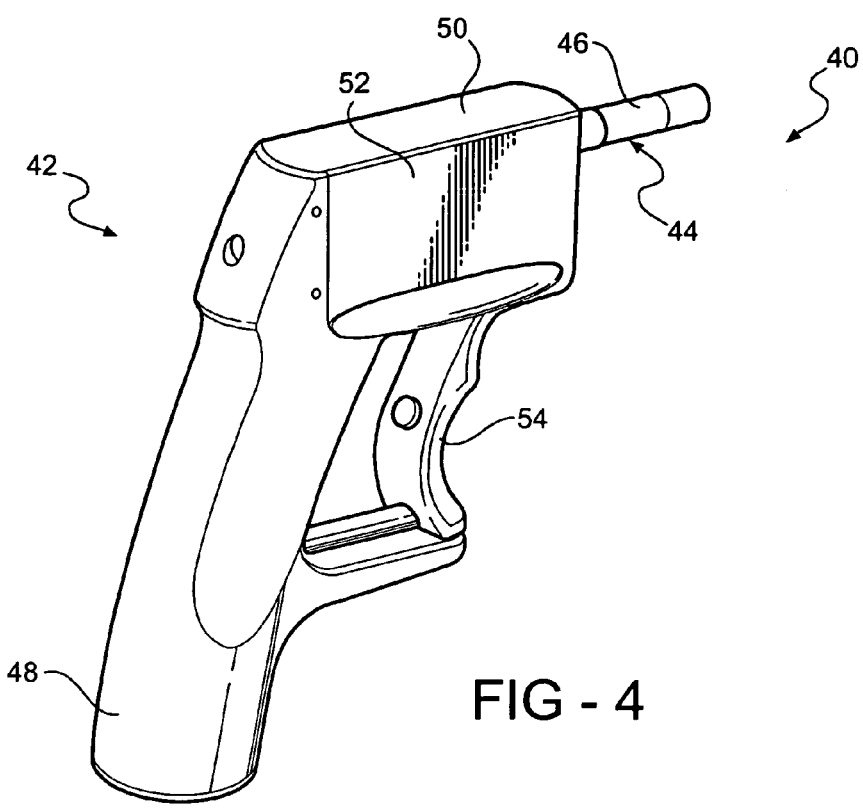
FIG. 4 is a side view of a first embodiment of a driving-in device according to the invention.

FIG. 4 shows a first embodiment of a driving-in device 40 according to the invention for the implant 10 according to FIGS. 1 to 3. The driving-in device 40 has the form of a gun with a gun body 42 and a gun barrel 44. The gun barrel 44 is formed by a receiving element 46 for holding the implant which is to be driven into place. The gun body 42 is formed by a handle 48 and a housing 50.

Arranged within the housing 50 is the driving-in mechanism, not shown in FIG. 4, which cooperates with the receiving element 46. The driving-in mechanism allows for the introduction of driving force into the receiving element 46.

The housing 50 comprises two laterally arranged and fully detachable housing covers. In the view according to FIG. 4, a single housing cover 52 can be seen. The detachable housing cover allows for easy cleaning and lubrication of the driving-in mechanism following the operation.

For the actuation of the driving-in mechanism, an operating mechanism in the form of a gun trigger 54 is provided. The gun trigger 54 has an ergonomic shape, which is adapted to actuation by means of index finger and middle finger or by means of middle finger and ring finger.

Figure 5:
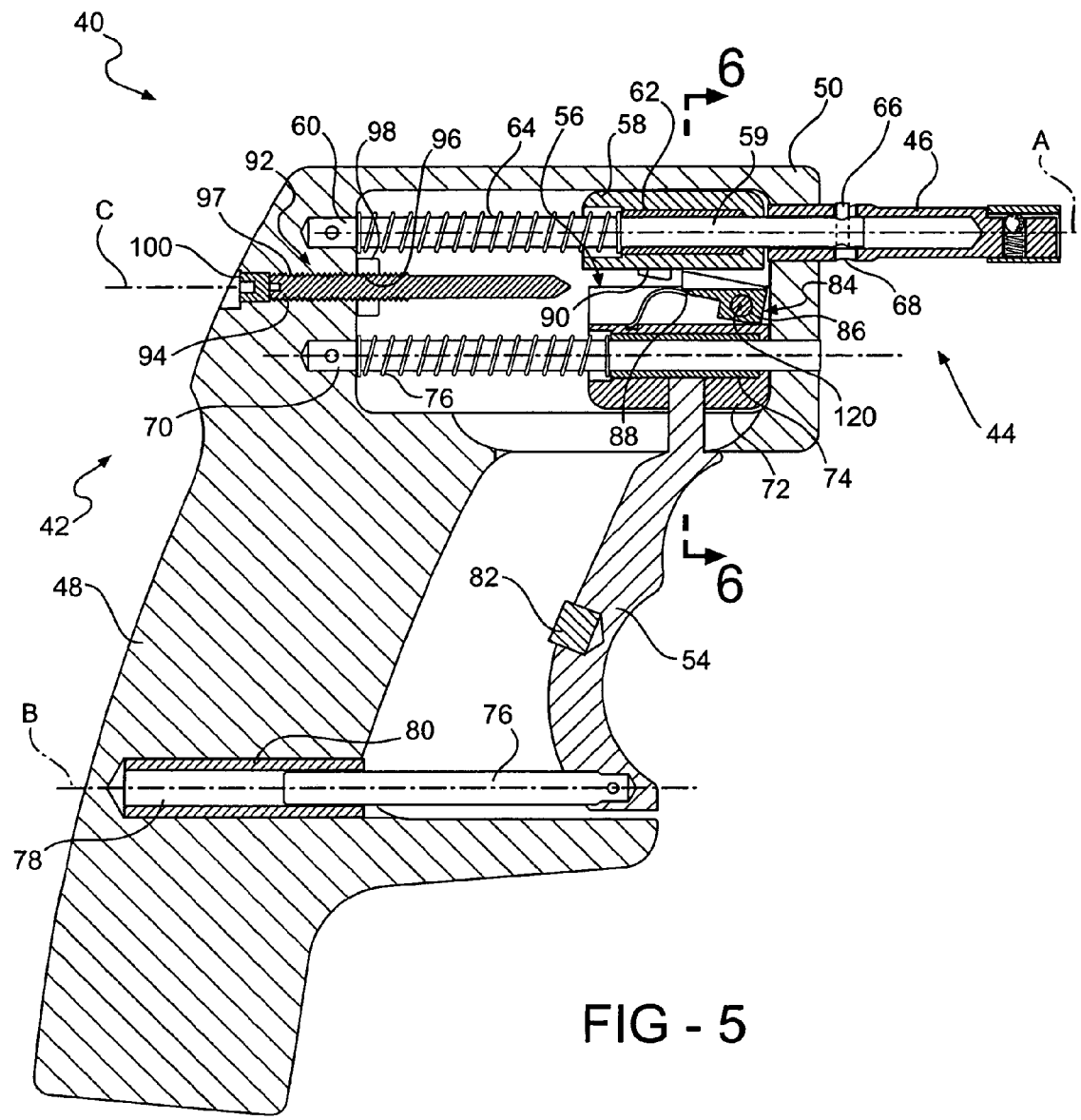
FIG. 5 is a longitudinal section through the driving-in device according to FIG. 4.

FIG. 5 is a longitudinal section through the driving-in device 40 according to FIG. 4 and in particular the driving-in mechanism 56 of the driving-in device 40.

The driving-in mechanism 56 is constructed as a striking mechanism and comprises a striking element in the form of an upper carriage 58. The upper carriage 58 comprises a central through aperture 59, through which a stationary, upper guide bolt 60 extends, which is anchored on the housing 50. The upper carriage 58 is displaceably guided by means of a ball implant 62 along the upper guide bolt 60.

The upper guide bolt 60 is radially enclosed on its outside by a helical spring 64, which in the starting position of the driving-in mechanism 56 illustrated in FIG. 5 rests with one end against the housing 50 and with its other end against the upper carriage 58. During a movement of the carriage along the upper guide bolt 60 to the left in FIG. 5, the helical spring 64 is compressed. At the same time, the upper carriage 58 is prestressed to the right in FIG. 5, i.e. in the driving-in direction.

The upper guide bolt 60 projects in the manner of a gun barrel partially out of the housing 50. At its end projecting from the housing 50, the upper guide bolt 60 is coupled with the receiving element 46 for the implant radially enclosing the said end on the outside. The coupling of the upper guide bolt 60 with the receiving element 46 is effected by means of a cross bolt 66 rigidly connected to the upper guide bolt 60. The cross bolt 66 projects through an opening 68 in the receiving element 46. The opening 68 is a slot having an oval shape and therefore allows for limited movement of the receiving element 46 relative to the upper guide bolt 60 along the axis A. The relative displaceability of the receiving sleeve is necessary in order to transmit the striking force introduced into the receiving sleeve 46 to the implant accommodated by the receiving element 46 and not illustrated in FIG. 5. The striking force is introduced into the receiving element 46 by means of the upper carriage 58 arranged coaxial to the receiving element 46.

Arranged within the housing 50 somewhat below the upper guide bolt 60 is a central guide bolt 70. The central guide bolt 70 is secured in a stationary manner in the housing 50 and extends parallel to the upper guide bolt 60. A lower carriage 72 is displaceably guided by a ball implant 74 along the central guide bolt 70, which penetrates the lower carriage 72. The central guide bolt 70 is enclosed radially on its outside by a helical spring 76, which is supported at one end against the housing 50 and at its other end against the lower carriage 72. During a displacement of the lower carriage 72 along the central guide bolt 70 to the left in FIG. 5, the helical spring 76 is compressed. At the same time, the lower carriage 72 is prestressed to the right in FIG. 5.

The lower carriage 72 is rigidly coupled with the gun trigger 54. Upon actuation of the gun trigger 54, i.e. during a displacement of the gun trigger 54 to the left in FIG. 5, the lower carriage is therefore also displaced to the left. Pressed into the gun trigger 54 is a plastics material plug 82. Upon actuation of the gun trigger 54, the plastics material plug 82 comes to rest against the gun handle 48 and thereby limits the displaceability of the gun trigger 54.

At its lower end in FIG. 5, the gun trigger 54 is connected to a lower guide bolt 76, which is displaceable relative to the housing 50. The lower guide bolt 76 is displaceably guided along an axis B in a blind bore 78 constructed in the piston handle 48. In order to reduce the frictional resistance, a plastics material sleeve 80 is pressed into the blind bore 78 which lines the blind bore 78 radially on the inside.

Provided within the housing 50 is a coupling device 84. The coupling device 84 allows for the coupling of the operating mechanism, i.e. the gun trigger 54, with the striking element in the form of the upper carriage 58. The coupling device 84 comprises a driver 86, which is pivotable in the plane of the drawing, a leaf spring 88 and a coupling element 90.

The driver 86 is pivotably secured to the lower carriage 72 and is prestressed in the direction of the upper carriage 58 by the leaf spring 88, which is also secured to the lower carriage 72. Arranged on the upper carriage 58 is the coupling element 90 cooperating with the driver 86.

Also accommodated within the housing 50 is a decoupling device 92, which can cooperate with the coupling device 84 and can release the coupling between the gun trigger 54 and the upper carriage 58. The decoupling device 92 comprises a pin 94 projecting into the housing 50. In order to render the decoupling threshold adjustable, the pin 94 is displaceable along its longitudinal axis C. To this end, the pin 94 comprises an external thread 96 radially on its outside, which cooperates with a matching internal thread 97 in the gun body 42. A counter nut 98 allows for locking of the pin 94 in a desired, axial position. At its end remote from the pin tip, the pin 94 is provided with an internal polygon allowing for the application of a tool to the pin 94 in order to adjust the decoupling threshold.

Figure 6:
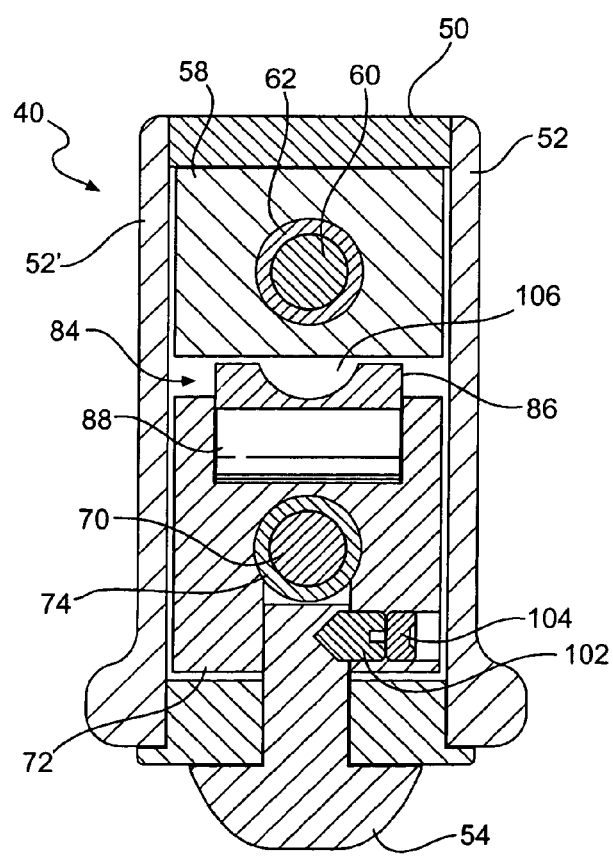
FIG. 6 is a cross section through the driving-in device according to FIG. 4 along the line VI-VI according to FIG. 5.

FIG. 6 is a cross section through the driving-in device 40 shown in FIG. 4 taken along the line IV-IV according to FIG. 5. As can be seen in FIG. 6, the housing 50 is closed laterally by two removable housing covers 52, 52'. Arranged within the housing 50 is the driving-in mechanism with the upper carriage 58 guided along the upper guide bolt 60 and the lower carriage 72 guided along the central guide bolt 70. The lower carriage 72 is connected by means of a screw 102 to the gun handle 54. The screw 102 comprises an internal polygon 104.

It can be clearly seen in FIG. 6 that the driver 86 of the coupling device 84 cooperating with the leaf spring 88 comprises a U-shaped groove 106. By means of this groove 106, the coupling device 84 cooperates with the pin 94 of the decoupling device. The groove 106 is arranged relative to the plane of the drawing in such a manner that the driver 86 can be forced downwards in FIG. 6 by the tip of the pin 94 against the spring force of the leaf spring 88.

Figure 7A:
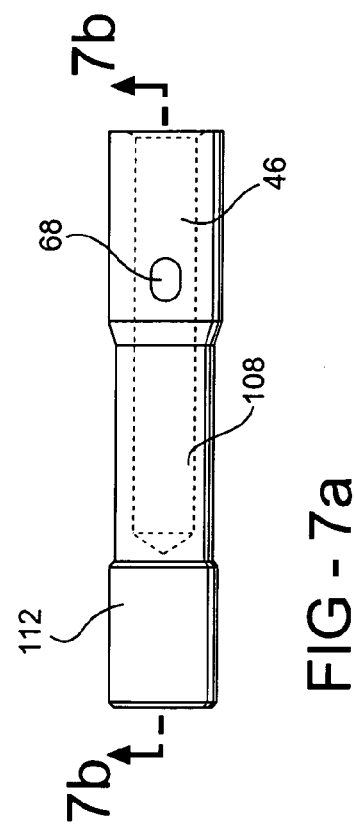
FIGS. 7a and 7b are a plan view and sectional view respectively of the receiving element for the implant.
Figure 7B:
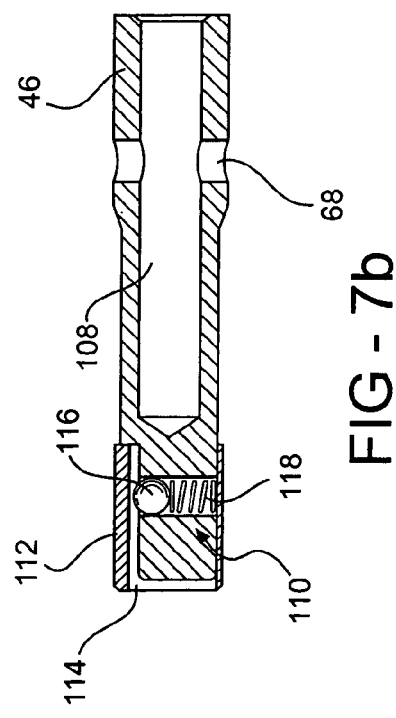

FIGS. 7a and 7b show the receiving element 46 of the driving-in device 40 illustrated in FIG. 4. Visible is the oval opening 68, in which the cross bolt 66 illustrated in FIG. 5 is displaceably guided. The receiving element 46 is partially constructed in the manner of a sleeve and comprises a blind bore 108 for receiving an end region of the upper guide bolt 60 illustrated in FIG. 5. At its end lying opposite the blind bore 108, the receiving element 46 comprises a sleeve 112, which radially encloses the cylindrical base element of the receiving element 46 on the outside. Formed between the cylindrical base element of the receiving element 46 and the sleeve 112 is a flat slot 114, which is used to receive the implant. The slot 114 can be seen in the sectional view according to FIG. 7b.

Arranged in the region of the slot 114 is a self-locking mechanism 110. The self-locking mechanism 110 comprises a ball 116 and a spring 118 prestressing the ball 116 in the direction of the slot 114. The ball 116 cooperates with the screw hole 26 of the implant 10 illustrated in FIG. 2.

The method of operation of the driving-in device 40 described above with reference to FIGS. 4 to 7b will be explained in further detail in the following.

In a first step, the implant 10 illustrated in FIGS. 1 to 3 is introduced with its left support arm 22 comprising the screw hole 26 into the slot 114 of the receiving element 46. As soon as the screw hole 26 lies in the region of the ball 116 prestressed in the direction of the slot 114, the ball 116 engages in the screw hole 26 and the self-locking mechanism 110 is actuated. Since the ball 116 engages with prestressing in the screw hole of the implant, it is no longer possible for the implant to accidentally slide out of the slot 114.

The implant is preferably directly removed from an implant container by means of the driving-in device 40. It is therefore unnecessary to introduce the implant into the slot 114 with the aid of the fingers. In this manner, the handling of the implant system according to the invention, comprising implant and driving-in device 40, is considerably improved.

Once the implant has been introduced into the slot 114 and has been secured there against falling out by means of the self-locking mechanism 110, the secured implant is positioned by means of the driving-in device 40 in the region of the bone cover or bone fragment which is to be fixed in place. The positioning is effected in such a manner that the right-hand support arm 24 of the implant 10 illustrated in FIG. 1 comes to rest upon the surface of the bone cover or bone fragment and the spike laterally contacts the spongious or cortical region.

Subsequently, the gun trigger 54 is displaced to the left in FIG. 5 by means of two fingers. This movement of the gun trigger 54 is also transmitted to the lower carriage 52 rigidly coupled with the gun trigger 54. Consequently, the lower carriage 52 moves to the left in FIG. 5 against the spring force of the helical spring 76.

As a result of the displacement of the lower carriage 72 to the left in FIG. 5, the driver 86 contacts the coupling element 90 of the upper carriage 58. As soon as the driver 84 contacts the coupling element 90, the upper carriage 58 is taken along by the driver 86 and is also displaced to the left in FIG. 5 against the spring force of the helical spring 64.

The coupling of the lower carriage 72 with the upper carriage 58 is recognized by the user of the driving-in device 40 in that the force required for the actuation of the gun trigger 54 increases. This increase in force results from the fact that it is now not only necessary to compress the lower helical spring 76, but also the upper helical spring 84, owing to the coupling of the lower carriage 72 and the upper carriage 58.

After a certain degree of displacement of the two carriages 72, 58, the pin 94 comes into contact with the groove 108 of the driver 86 illustrated in FIG. 6. With a further displacement of the two carriages 58, 72 to the left in FIG. 5, the driver 86 is now pivoted downwards by the inclined surface of the tip of the pin 94 about its pivot axis 120 illustrated in FIG. 5 against the spring force of the leaf spring 88. Finally, once a threshold pivoting angle is reached, the coupling between the driver 86 and the coupling element 90 of the upper carriage 58 is abruptly released. As a result of the decoupling of the lower carriage 72 and upper carriage 58, the upper carriage 58 prestressed to the right in FIG. 5 by the helical spring 64 is accelerated to the right in FIG. 5 along the upper guide piston 60. The accelerated upper carriage 58 comes into striking contact with the end face facing the upper carriage 58 of the receiving element 46, which has been slightly displaced along the axis A, and exerts a blow to the said end face.

This blow is transmitted to the implant 10 arranged in the slot 114, the spike 16 of the implant 10 thereby being laterally driven into the bone cover or bone fragment. During the driving-in, the implant arm 24 of the implant 10 resting upon the bone cover or bone fragment acts as a guide.

As soon as the upper carriage 58 is decoupled from the lower carriage 72, the gun trigger 54 can be released again. Following the release of the gun trigger 54, the compressed helical spring 76 expands again and the gun trigger 54 is moved by the helical spring 76 back into the starting position illustrated in FIG. 5. The driving-in procedure described above can then be repeated, if necessary, to drive the spike 16 of the implant 10 deeper into position. As soon as the extension 14 rests laterally against the bone cover or bone fragment, the driving-in procedure is complete. The extension 14 then functions as a mechanical abutment, which prevents the spike 16 from being driven too deeply into the bone cover.

It is usually necessary to position three to four implants 10 according to FIGS. 1 to 3 in a bone cover in order to reliably fix the bone cover in the skull bone. Once the required number of implants have been driven into the bone cover, the bone cover is positioned in the corresponding opening in the skull bone and is secured to the skull bone by means of a bone screw for each implant. This is illustrated in further detail in FIG. 9, which will be described in more detail below.

Figure 8:
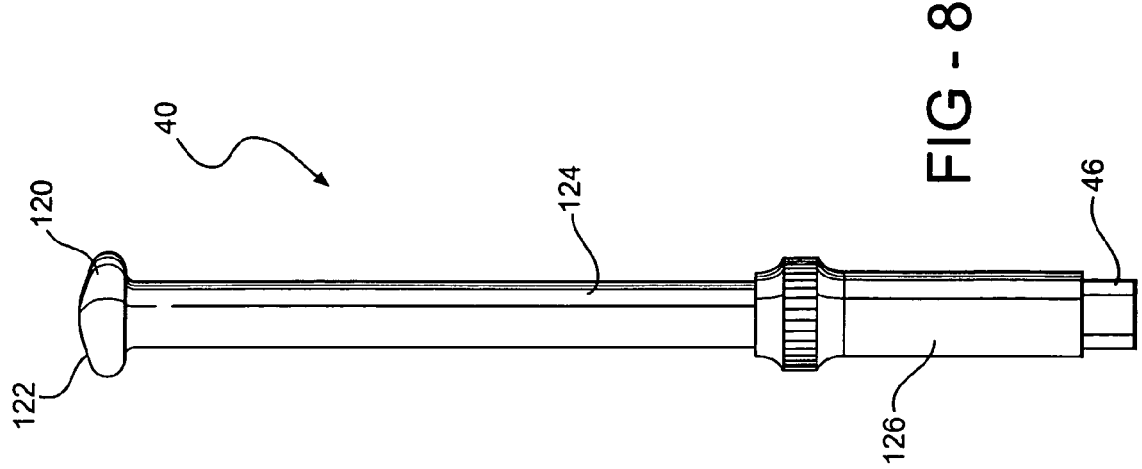
FIG. 8 is a plan view of a second embodiment of a driving-in device according to the invention.

FIG. 8 shows a second embodiment of a driving-in device 40 according to the invention for driving an implant laterally into a bone cover or bone fragment. The driving-in device 40 has an elongated structure and comprises a receiving element 46 for the implant as well as a knob-like force-receiving structure 120 having a spherically curved force-receiving surface 122. The driving-in device 40 also comprises a substantially cylindrical body 124, which is arranged in a force-transmitting manner between the force-receiving structure 120 and the receiving element 46 for the implant. At its end facing the receiving element 46, the cylindrical element 124 comprises a grip 126, which radially encloses the outside of the cylindrical body 124. The grip 126 is coupled to the body 124 so as to be immovable in the axial direction. The receiving element 46 comprises the self-locking mechanism illustrated in FIGS. 7a and 7b for the implant.

In order to secure the implant to a bone plate, for example, the implant is firstly fixed in the region of the receiving element 46 by means of the self-locking mechanism. The implant is then positioned as described above and a striking force is introduced into the force-receiving surface 122 of the force-receiving structure 120 by means of a hammer, for example. The striking force is transmitted from the force-receiving structure 120 via the body 124 and the receiving element 46 to the implant 10, which is thereby driven laterally into the bone cover.

Figure 9:
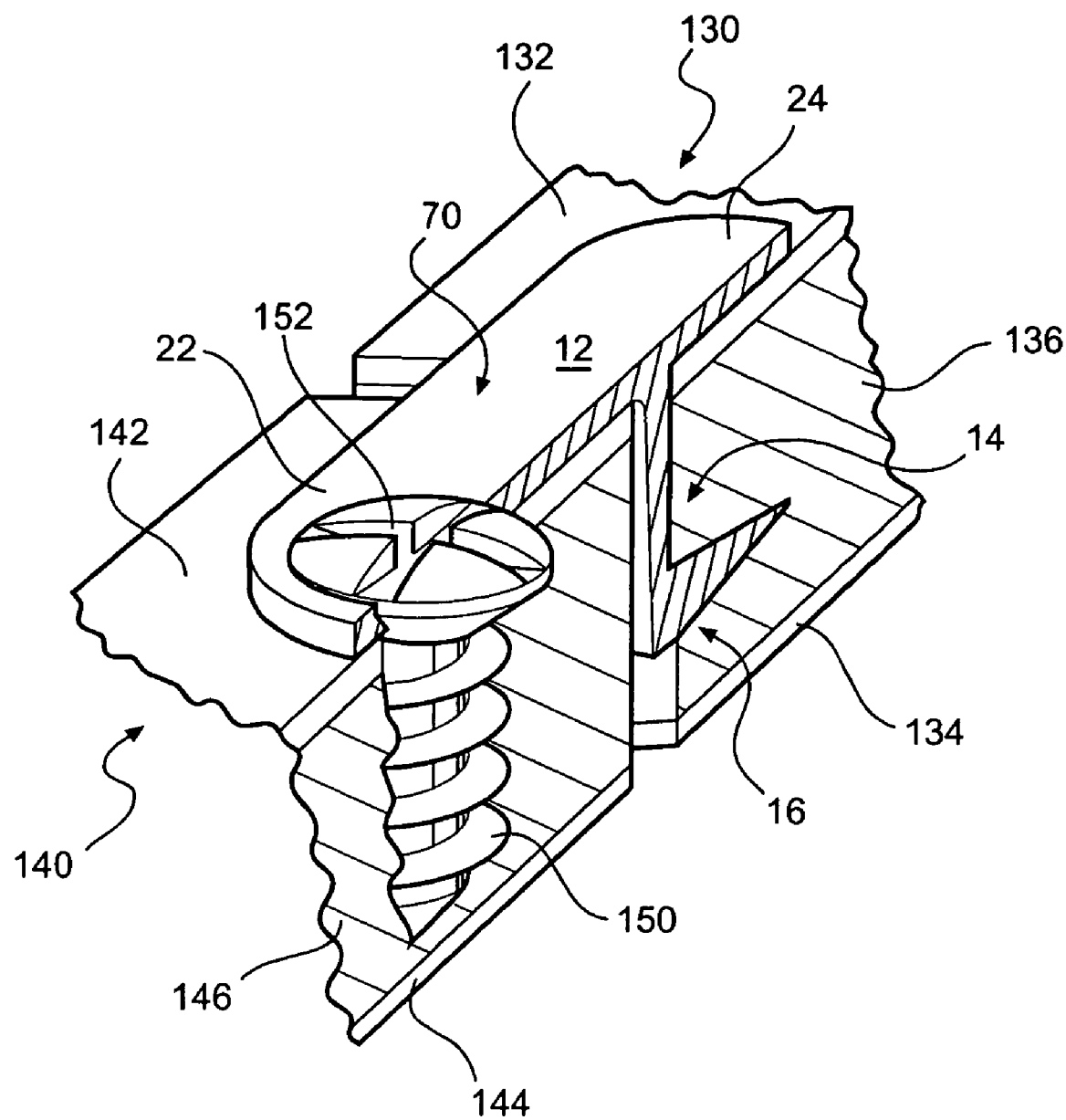
FIG. 9 is a perspective view of the driven-in implant according to FIG. 1 following its securing in the skull bone.

FIG. 9 shows a bone cover 130, which comprises an upper bone plate 132 (first cortical layer), a lower bone plate 134 (second cortical layer) as well as a spongious region 136 arranged between the upper bone plate 132 and the lower bone plate 134. The implant 10 has been secured to the bone cover 130 by means of the driving-in device 40 described with reference to FIGS. 4 to 7b. The spike 16 of the implant 10 has been driven into the spongious region 136 of the bone cover 130 to such a depth that the extension 14 rests laterally against the bone cover 130.

Following the securing of a plurality of implants 10 to the bone cover 130, the bone cover 130 was positioned in the corresponding opening in the skull bone 140. In this respect, the underside of the support arm 22 of the implant 10 comes to rest against the upper bone plate 142 of the skull bone 140. The skull bone 140 also comprises a spongious region 146, which is arranged between the upper bone plate 142 and a lower bone plate 144.

Following the positioning of the bone cover 130 provided with the implant 10 in the opening of the skull bone 140, the bone cover 130 needs to be fixed in position within the opening of the skull bone 140. To this end, the implants 10 are secured to the skull bone 140 by means of bone screws 150. During this process, the spherical head 152 of each bone screw 150 is fully recessed within the screw hole of the implant 10.

In the case of bicortical bones such as the bone cover 130 illustrated in FIG. 9, it is expedient to drive the spike 16 of the implant 10 into the spongious region arranged between the two cortical layers. However, the driving of the spike 16 into a cortical layer is also possible and might even be essential, e.g. in the case of mono-cortical bones.

The invention claimed is:

1. A system for attaching a bone cover or a bone fragment to a skull, the system comprising:
   an implant including:
      a support element having an upper side and a lower side;
      an extension extending substantially at a right angle from the lower side of the support element to an end remote from the support element and substantially straight between the support element and the end; and
      at least one spike extending substantially parallel to the support element such that the spike can be driven laterally into the bone cover or bone fragment prior to positioning the bone cover or bone fragment adjacent to the skull,
      wherein the support element comprises two support arms extending in opposite directions from the extension with the first of the two support aims defining a screw hole therein for receiving a fastener to secure the first support arm to the skull after the spike has been driven laterally into the bone cover or bone fragment and after positioning the bone cover or bone fragment adjacent to the skull and the second of the two support arms for cooperating with the bone cover or bone fragment when driving the spike laterally into the bone cover or bone fragment,
   an implant delivery device including:
      a body;
      a receiving element supported by the body and defining a receiving structure at one end thereof for receiving the implant;
      a driving-in mechanism operative with the receiving element for driving the at least one spike of the implant laterally into the bone cover or bone fragment; and
      an operating mechanism coupled to the body to actuate the driving-in mechanism.

2. The system according to claim 1, wherein the lower side of the support element is concave or spherically curved at least in sections.

3. The system according to claim 1, wherein the spike is disposed at the end of the extension remote from the support element and extends from the end of the extension remote from the support element.

4. The system according to claim 1, wherein the support element has a thickness increasing in the direction of the screw hole.

5. The system according to claim 1, wherein an inside of the screw hole is spherically curved.

6. The system according to claim 1, wherein the spike extends from the extension in a same direction as the second support arm and cooperates with the second support arm and the bone cover or bone fragment to anchor the implant.

7. The system according to claim 1, wherein the spike has a substantially triangular form.

8. The system according to claim 7, wherein the second support arm extends in a same direction as the substantially triangular spike and cooperates with the substantially triangular spike and the bone cover or bone fragment to anchor the implant.

9. The system according to claim 1, wherein the extension is inelastic such that the extension extends rigidly from the lower side of the support element.

10. The system according to claim 6, wherein the second support arm has a length and the spike extends from the extension more than one half the length of the second support arm to anchor the implant.

11. The system according to claim 1, wherein the second support arm has a length and the spike extends from the extension more than one half the length of the second support arm to anchor the implant.

12. The system according to claim 11, wherein the upper side of the support element is continuous across the second support arm such that the second support arm is free of any screw hole.

13. A method of attaching a bone cover or a bone fragment to a skull with a self-retaining implant comprising a support element having a lower side, an extension extending substantially at a right angle from the lower side of the support element to an end remote from the support element and substantially straight between the support element and the end, and at least one spike extending substantially parallel to the support element, wherein the support element includes two support arms extending in opposite directions from the extension with the first of the two support arms defining a screw hole therein for receiving a fastener and the second of the two support arms for cooperating with the bone cover or bone fragment, said method comprising the steps of:
   providing an implant delivery device including a body, a receiving element supported by the body and defining a receiving structure at one end thereof to receive the implant, a driving-in mechanism operative with the receiving element for driving the spike laterally into the bone cover or bone fragment, and an operating mechanism coupled to the body to actuate the driving-in mechanism;
   positioning the implant in the receiving structure of the receiving element;
   actuating the driving-in mechanism and driving the spike laterally into the bone cover or bone fragment;
   positioning the bone cover or bone fragment adjacent to the skull after driving the spike laterally into the bone cover or bone fragment; and
   securing the first support arm to the skull after positioning the bone cover or bone fragment adjacent to the skull.

14. The system according to claim 1, wherein the receiving element includes an end such that a striking force can be applied to the receiving element end by the driving-in mechanism.

15. The system according to claim 1, wherein the driving-in mechanism comprises a striking element displaceable against a spring force.

* * * * *